United States Patent
Karami et al.

(10) Patent No.: US 12,138,363 B2
(45) Date of Patent: Nov. 12, 2024

(54) CROSS-LINKABLE POLYMER, HYDROGEL, AND METHOD OF PREPARATION THEREOF

(71) Applicant: ÉCOLE POLYTECHNIQUE FÉDÉRALE DE LAUSANNE (EPFL), Lausanne (CH)

(72) Inventors: Peyman Karami, Lausanne (CH); Dominique Pioletti, Buchillon (CH); Céline Samira Wyss, Chavannes-Renens (CH); Pierre-Etienne Bourban, Nyon (CH); Christophe Moser, Lausanne (CH)

(73) Assignee: ÉCOLE POLYTECHNIQUE FÉDÉRALE DE LAUSANNE, (EPFL) Lausanne (CH)

(*) Notice: Subject to any disclaimer, the term of this patent is extended or adjusted under 35 U.S.C. 154(b) by 799 days.

(21) Appl. No.: 17/282,154

(22) PCT Filed: Oct. 4, 2019

(86) PCT No.: PCT/EP2019/076874
§ 371 (c)(1),
(2) Date: Apr. 1, 2021

(87) PCT Pub. No.: WO2020/070267
PCT Pub. Date: Apr. 9, 2020

(65) Prior Publication Data
US 2022/0031909 A1 Feb. 3, 2022

(30) Foreign Application Priority Data
Oct. 4, 2018 (WO) .................. PCT/EP2018/077045

(51) Int. Cl.
*A61L 27/20* (2006.01)
*A61L 27/52* (2006.01)
(Continued)

(52) U.S. Cl.
CPC ................ *A61L 27/20* (2013.01); *A61L 27/52* (2013.01); *C08B 37/0072* (2013.01);
(Continued)

(58) Field of Classification Search
None
See application file for complete search history.

(56) References Cited

U.S. PATENT DOCUMENTS

2002/0120333 A1  8/2002  Keogh et al.
2011/0008443 A1*  1/2011  Alsberg .................. A61L 27/38
977/773
(Continued)

FOREIGN PATENT DOCUMENTS

CN  105358675 A  2/2016
CN  107011609 A  8/2017
(Continued)

OTHER PUBLICATIONS

Tamesue et al., "Highly tolerant and durable adhesion between hydrogels utilizing intercalation of cationic substituents into layered inorganic compounds," ACS Macro Letters, 2016, pp. 704-708, vol. 5.
(Continued)

*Primary Examiner* — Peter A Salamon
(74) *Attorney, Agent, or Firm* — The Webb Law Firm

(57) ABSTRACT

The invention relates to a cross-linkable polymer including a base polymer including functional groups at least some of which have been reacted with a first organic molecule including a cross-linkable unit and with a second organic molecule capable of bonding to organic and/or inorganic substrates. The invention further relates to a hydrogel including the cross-linkable polymer that includes cross-linkable polymer strands, wherein at least some of the cross-linkable units of different cross-linkable polymer
(Continued)

strands have reacted to form a covalent bond thereby forming a covalently linked network. The invention further relates to a method for the preparation of the hydrogel and to the use of the hydrogel.

26 Claims, 5 Drawing Sheets

(51) Int. Cl.
C08B 37/08 (2006.01)
C08J 3/075 (2006.01)

(52) U.S. Cl.
CPC .......... *C08J 3/075* (2013.01); *A61L 2430/02* (2013.01); *A61L 2430/06* (2013.01); *C08J 2305/08* (2013.01)

(56) References Cited

U.S. PATENT DOCUMENTS

| | | | | |
|---|---|---|---|---|
| 2014/0044786 A1* | 2/2014 | Wilding | ............... | A61P 25/20 |
| | | | | 514/253.07 |
| 2014/0120185 A1* | 5/2014 | Hirose | ............... | A61K 31/137 |
| | | | | 514/252.19 |
| 2014/0144684 A1* | 5/2014 | Saitou | ............... | H05K 1/095 |
| | | | | 427/98.5 |
| 2016/0067378 A1* | 3/2016 | Wagner | ............... | A61L 24/08 |
| | | | | 514/23 |
| 2016/0116453 A1 | 4/2016 | Lutolf et al. | | |
| 2017/0216485 A1 | 8/2017 | Wang et al. | | |
| 2017/0312306 A1 | 11/2017 | Ranatunga et al. | | |
| 2022/0031909 A1* | 2/2022 | Karami | ............... | A61L 27/52 |

FOREIGN PATENT DOCUMENTS

| | | | |
|---|---|---|---|
| CN | 108264611 A | 7/2018 | |
| DE | 0415183 A2 * | 8/1989 | ............ A61L 15/16 |
| WO | 2014046415 A1 | 3/2014 | |

OTHER PUBLICATIONS

Xu et al., "Mollusk glue inspired mucoadhesives for biomedical applications," Langmuir, 2012, pp. 14010-14017, vol. 28:39.

Guvendiren et al., "Self-assembly and adhesion of DOPA-modified methacrylic triblock hydrogels," Biomacromolecules, 2008, pp. 122-128, vol. 9:1.

Kurokawa et al., "Formation of a strong hydrogel-porous solid interface via the double-network principle," Acta Biomaterialia, 2010, pp. 1353-1359, vol. 6:4.

Lee et al., "Mussel-inspired adhesives and coatings," Annual Review of Materials Research, 2011, pp. 99-132, vol. 41.

Lee et al., "Single-molecule mechanics of mussel adhesion," Proceedings of the National Academy of Sciences of the United States of America, 2006, pp. 12999-13003, vol. 103:35.

Lee et al., "Synthesis of 3,4-dihydroxyphenylalanine (DOPA) containing monomers and their co-polymerization with PEG-diacrylate to form hydrogels," Journal of Biomaterials Science Polymer Edition, 2004, pp. 449-464, vol. 15:4.

Li et al., "Tough adhesives for diverse wet surfaces," Science, 2017, pp. 378-381, vol. 357.

Liu et al., "Injectable dopamine-modified poly(ethylene glycol) nanocomposite hydrogel with enhanced adhesive property and bioactivity," ACS Applied Materials & Interfaces, 2014, pp. 16982-16992, vol. 6.

Strehin et al., "A versatile pH sensitive chondroitin sulfate-PEG tissue adhesive and hydrogel," Biomaterials, 2010, pp. 2788-2797, vol. 31:10.

Yuk et al., "Tough bonding of hydrogels to diverse non-porous surfaces," Nature Materials, 2016, pp. 190-196, vol. 15:2.

Zhao, X., "Multi-scale multi-mechanism design of tough hydrogels: building dissipation into stretchy networks," Soft Matter, 2014, pp. 672-687, vol. 10:5.

Park et al., Catechol-Functionalized Hyaluronic Acid Hydrogels Enhance Angiogenesis and Osteogenesis of Human Adipose-Derived Stem Cells in Critical Tissue Defects, Biomacromolecules, 2016, pp. 1939-1948, vol. 17(6).

Abbott, S., Adhesion Science: Principles and Practice, 2015, pp. 52-55, DEStech Publications, Lancaster, Pennsylvania.

Neto et al., "Nanostructured Polymeric Coatings Based on Chitosan and Dopamine-Modified Hyaluronic Acid for Biomedical Applications, " Small, 2014, pp. 1-11.

* cited by examiner

CROSS-LINKABLE POLYMER, HYDROGEL, AND METHOD OF PREPARATION THEREOF

CROSS-REFERENCE TO RELATED APPLICATIONS

This application is the United States national phase of International Application No. PCT/EP2019/076874 filed Oct. 4, 2019, and claims priority to International Application No. PCT/EP2018/077045 filed Oct. 4, 2018, the disclosures of which are hereby incorporated by reference in their entirety.

BACKGROUND OF THE INVENTION

Field of the Invention

The invention relates to a cross-linkable polymer comprising a base polymer, a hydrogel comprising the cross-linkable polymer, a method for the preparation of the hydrogel, and the use of the hydrogel.

Description of Related Art

Hydrogels have become increasingly important in biomedical applications such as in the treatment of cartilage damage. For biomedical applications, hydrogels desirably show good adhesion, in particular to biological surfaces.

Double network hydrogels are normally formed by two networks with different chemical composition. The two networks may each be covalently crosslinked or one of the networks may be covalently cross-linked network and the other one may be physically cross-linked. For example, a mixture of poly(ethylene glycol) dimethacrylate and alginate forms a double network in which the poly(ethylene glycol) dimethacrylate forms the covalently linked network after cross-linking and the alginate forms the physically cross-linked network. So far, the majority of research efforts have proposed different strategies to increase adhesion, mainly by the improvement of interfacial interactions (see Xu J. et al. in Langmuir 28, 14010-14017 (2012); Liu, Y. et al. in ACS Applied Materials & Interfaces 6, 16982-16992 (2014); Strehin, I. et al. in Biomaterials 31, 2788-2797 (2010); Guvendiren, M. et al. Biomacromolecules 9, 122-128 (2008); Tamesue, Sh. Et al. in ACS Macro Lett 5, 704-708 (2016)). However, with this approach, the obtained adhesion improvement is often quite insignificant (Abbott, S. in Adhesion Science: Principles and Practice, DEStech Publications, (2015)).

In addition to these strategies, a few hydrogel systems have been proposed with interestingly high adhesive properties based on tuning the dissipative properties of hydrogels recently (Yuk, H. et al. in Nature Materials 15, 190-196, (2016)). However, good adhesion of these systems is not easily achieved as the robust bonding of these hydrogel systems requires surface modification of solids, (Li, J. et al. in Science 357, 378-381 (2016)) porous surface structure (Kurokawa, T. et al. in Acta Biomaterialia 6, 1353-1359 (2010)), or inorganic solid surfaces, which is clearly not suitable to biological surfaces and clinical applications.

Although the integration of a dissipative network into soft tissue surfaces such as hydrogels was shown to increase adhesion strength to unprecedented values, several limitations in the hydrogel performance as a biomaterial remain. First, the tissue surface is the dominant part for the attachment of the hydrogel to the tissue. This means that the quality of the interface mainly depends on the chemistry and morphology of the tissue surface. Therefore, it is not possible to obtain sufficient adhesion on many biological surfaces. Second, the swelling ratio of a hydrogel can be very high, which imposes serious limitations on many biomedical applications as well as maintaining hydrogel properties. Third, from a practical point of view, the processability of the hydrogel should be highly improved in order to use it in an application. Fourth, the interface design is not effectively included in the proposed hydrogel design.

It has been shown that a short chain network often results in a hydrogel with a higher stiffness than a hydrogel with a long chain network. However, a short chain network may be fractured or the crosslinks may be broken on deformation. On the other hand, longer chains can improve the mobility of the system, which contributes to high energy transfer (Zhao, X. in Soft Matter 10, 672 (2014)). It would be desirable to accommodate the two counteracting effects described above in a hydrogel. In particular, it would be desirable to allow for a balance between stiffness, particularly provided by a short chain network, and mobility, in particular provided by a long chain network, in a hydrogel. Moreover, these two parameters may both be required for a tough hydrogel, and consequently a tough interface.

The adhesion analysis of double-network hydrogels has shown that anchoring a covalently crosslinked network to a surface often gives higher interfacial toughness than anchoring a physically crosslinked dissipative network, unless there are strong interactions between the covalently and the physically crosslinked networks (Yuk, H. et al. in Nature Materials 15, 190-196, (2016)). As a result, it seems that effective adhesion of the hydrogel to a surface requires the possibility for local deformations and the transfer of energy, such as deformation energy, away from the attaching contact points between the hydrogel and the surface. Although dissipative mechanisms contribute to energy transfer to a larger extent around the interface through the first network, the contribution of attaching chains to energy transfer should be more significant, particularly for double network hydrogels without strong interactions between the networks.

The adhesive performance of marine mussels has provided important chemical and physical understanding into adhesion phenomenon on wet surfaces. Water could cause adhesive failure, especially in biological environments rather than on dry surfaces, through weakening interfacial bondings, swelling, etc. However, the adhesion mechanism of marine mussels allows strong attachment to different surfaces in wet environments (Bruce, P., et al. in Annual Review of Materials Research 41, 99-132 (2011)).

There are several proteins in the byssal plaque of the mussel. All these proteins contain the post-translationally modified amino acid 3,4-dihydroxyphenyl-L-alanine (hereinafter "Dopaacid") and have widely different sequences. It is well discussed that the presence of this amino acid is responsible for the mussel's ability to stick, in particular to various surfaces. The key part of this modified amino acid appears to be the catechol side-chain, made up of a benzene ring with two hydroxyl groups which is said to be able to form bonds with different surfaces (Lee, H., et al. in PNAS 103, 12999-13003 (2006)).

The primary adhesive interactions of mussel with the surface is commonly attributed to the presence of mussel foot protein-3 (hereinafter Mfp-3) and mussel foot protein-5 (hereinafter Mfp-5). Dopaacid content in these two proteins is much higher than in the other proteins (Lee, H., et al. in Annu Rev Mater Res 41, 99-132 (2011)).

Molecular-level studies of Dopaacid interfacial behavior revealed strong and reversible interactions between Dopaacid and inorganic surfaces. According to these studies, the strength of the interaction between Dopaacid and an oxide surface at high pH lead to lower pull-off forces, due to auto-oxidation of Dopaacid to its quinone form (hereinafter also "Dopaacidquinone") at alkaline pH. Dopaacid interaction with inorganic surfaces is stronger in the catechol form compared with the quinone form. However, Dopaacidquinone may be able to contribute to interfacial bonding with organic surfaces by covalent reactions between quinones and nucleophiles on organic surfaces. For example, covalent bonding could form between Dopaacid and primary amine at high pH (Lee, H. in PNAS 103, 12999-13003 (2006)).

For biomedical applications, hydrogels should present sufficient adhesive properties to the biological surfaces. It is also desirable that hydrogels present a tunable swelling ratio. Hydrogels should also be biocompatible to allow for their use in biological systems. Moreover, hydrogels should be processable so that their use can be easily implemented. For many applications, it is also desirable that the hydrogel has a controllable biodegradability. Moreover, a high water content is also desirable for many applications. In addition, there are other applications of hydrogels for which properties such as cell encapsulation, delivery of cells, delivery of proteins such as growth factors/cytokines or drugs as well as cell adhesion are desirable.

The properties described above impose serious limitations on the adhesive hydrogels known in the prior art. For example, cell inclusion should not impact hydrogel mechanics. Therefore, an object of the present invention is to provide a hydrogel, in particular an adhesive hydrogel, that is able to satisfy at least some of the application requirements and specifications described above. In particular, a hydrogel with tunable bulk and tunable adhesive properties would be desirable.

It is a particular object of the invention to provide a stiff adhesive-containing polymeric structure which is both able to be crosslinked with strong covalent bonding and to be strongly attached to biological surfaces.

Other objects and more specific objects will in part be apparent and will in part appear hereinafter.

SUMMARY OF THE INVENTION

Some or all of these objects are achieved by the cross-linkable polymer as described herein.

The invention provides for a cross-linkable polymer comprising a base polymer comprising functional groups at least some of which have been reacted with a first organic molecule comprising a cross-linkable unit and with a second organic molecule capable of bonding to organic and/or inorganic substrates.

In the cross-linkable polymer according to the invention, the base polymer is reacted with a first organic molecule and with a second organic molecule. Preferably, in the cross-linkable polymer according to the invention, the base polymer is first reacted with the first organic molecule and the resulting polymer is then reacted with the second organic molecule.

Surprisingly it was found that with a cross-linkable polymer comprising a base polymer comprising functional groups at least some of which have been reacted with a first organic molecule comprising a cross-linkable unit and with a second organic molecule capable of bonding to organic and/or inorganic substrates, hydrogels with a low swelling ratio and a good elastic modulus can be obtained. As a result, these hydrogels display good adhesion, in particular to biological surfaces, in particular biological tissues, such as articular cartilage or meniscus.

Without wishing to be bound by scientific theory it is believed that the hydrogel formed with the cross-linkable polymer of the present invention allows for good energy transfer by forming a dissipative cross-linked network. Moreover, it is believed that the low swelling ratio of the hydrogel further aids in good adhesion, in particular to biological surfaces. It is further believed that the chains of the hydrogel that are anchored to a biological tissue surface can maintain a high stiffness of the hydrogel. The energy may be transferred from the interfacial contact points to the hydrogel network. These factors are believed to be the main contributors in the hydrogel structure to allow the hydrogel to create a high-strength interface and to adhere to a wide range of biological surfaces.

In the present invention, the term "hydrogel" encompasses gels that comprise water, buffer such as hepes buffer or phosphate buffered saline, alcohol, or mixtures thereof, in particular that comprise water, buffer such as hepes buffer or phosphate buffered saline, or mixtures thereof.

Unless otherwise stated, phosphate buffered saline is an aqueous solution comprising from 0.130 mol/L to 0.160 mol/L, in particular from 0.135 mol/L to 0.155 mol/L, more particularly 0.137 mol/L, of sodium chloride, from 0 mol/L to 0.0029 mol/L, in particular 0.0027 mol/L, of potassium chloride, and from 0.0004 mol/L to 0.012 mol/L, in particular from 0.010 mol/L to 0.012 mol/L, more particularly 0.012 mol/L of phosphate, including $HPO_4^{2-}$ and $H_2PO_4^-$, at a pH of from 5.5 to 9.5, in particular from 7 to 8, more particularly at 7.4. Unless otherwise stated, hepes buffer is an aqueous solution comprising from 0.1 mol/L to 1 mol/L, in particular 1 mol/L, hepes, wherein hepes is in particular 2-(4-(2-hydroxyethyl)-piperazin-1-yl)-ethanesulfonic acid.

The cross-linkable polymer comprises a base polymer comprising functional groups. Some or all of the functional groups of the base polymer may undergo a reaction with an organic molecule. In this way, at least some of the functional groups may be transformed by covalently attaching an organic residue. As a result, the base polymer may be functionalized. The functional groups may interact via non-covalent interactions. The non-covalent interactions may also be intermolecular interactions. As a result non-covalent bonds may form between different polymer strands that may aid in network formation via non-covalent bonds.

The first organic molecule and the second organic molecule are preferably covalently attached to the base polymer, in particular via the functional groups of the base polymer. It is possible that an organic residue originating from the first organic molecule is covalently attached to the base polymer. It is also possible that an organic residue originating from the second organic molecule is covalently attached to the base polymer. For example, when using methacryloyl chloride as the first organic molecule, the organic residue methacryloyl is covalently attached to a functional group of the base polymer. Similarly, when using (2-chlorocarboxyethyl) phosphonic acid diethyl ester as the second organic molecule, the organic residue 3-Diethoxyphosphorylpropionyl is covalently attached to a functional group of the base polymer.

The base polymer may comprise various functional groups. In particular, the base polymer may comprise more than one type of functional groups. Preferably, the base polymer comprises at least one of hydroxyl groups, amine groups, carboxylic acid groups, amide groups, and thiol groups. These functional groups allow for a good functionalization or for the formation of strong non-covalent interactions. More preferably, the base polymer comprises hydroxyl groups, amide groups and carboxylic acid groups.

Different polymers may be used as the base polymer. Advantageously, the base polymer is hydrophilic. Preferably, the base polymer or a salt thereof is water soluble. The base polymer or a salt thereof is in particular considered to be water soluble if 1 g of the base polymer or a salt thereof dissolves at 25° C. in 200 mL water or less. It is also possible that a mixture of polymers is used as the base polymer. Preferably, the base polymer is selected from the group consisting of hyaluronic acid, alginate, chitosan, pectine, poly(ethylene glycol), carboxymethyl cellulose, poly(vinyl alcohol), poly(2-hydroxyethyl methacrylate), poly(acrylamide), fibrin, silk, collagen, and mixtures thereof. With these polymers, hydrogels with good stiffness and low swellability can be obtained by reacting at least some of the functional groups with a first organic molecule and a second organic molecule as described herein. More preferably, the base polymer is hyaluronic acid.

The cross-linkable polymer according to the invention comprises a base polymer comprising functional groups at least some of which have been reacted with a first organic molecule comprising a cross-linkable unit. With the aid of the cross-linkable unit, a covalent network may be formed in the hydrogel according to the invention. Different cross-linkable units may be used according to the invention. For example, cross-linkable units that can undergo a reaction with an initiator such as a radical initiator may be used. After reacting with the radical initiator, the cross-linkable unit may then react with another cross-linkable unit. Further, cross-linkable units that may undergo a reaction upon activation with an external stimulus such as UV radiation or X-ray radiation may be used. Further, the cross-linkable unit may also undergo a reaction with a cross-linker molecule such as a diamine. Preferably, the cross-linkable unit of the first organic molecule comprises at last one of a carbon-carbon double bond (—C=C—), a thiol group (—SH), an epoxide group, and an acid anhydride group. More preferably, the cross-linkable unit consists of one of these groups. With these cross-linkable units, the reliable formation of covalent networks has been achieved. More preferably, the cross-linkable unit of the first organic molecule comprises or consists of a carbon-carbon double bond.

The first organic molecule may comprise more than one, in particular two or three, cross-linkable units. Also, the organic residue that is covalently attached to the base polymer as a result of the reaction of the base polymer with the first organic molecule may comprise more than one, in particular two or three cross-linkable units. Preferably, the organic residue that is covalently attached to the base polymer as a result of the reaction of the base polymer with the first organic molecule comprises one cross-linkable unit.

Advantageously, the first organic molecule comprises an attachment unit. The attachment unit particularly allows the attachment of the first organic molecule to the functional groups of the base polymer. After reaction of the first organic molecule with a functional group of the base polymer, the attachment unit may be transformed into a different group. For example, the first organic molecule may comprise an acid chloride group as an attachment unit that may be transformed into an ester or an amide group upon reaction with a hydroxyl or an amine group as the functional groups of the base polymer. Preferably the attachment unit of the first organic molecule is selected from the group consisting of an aldehyde group, an acid chloride group, an acid anhydride group, a carboxylic acid group, an amine group, a catechol group, and a hydroxyl group. These units have shown to allow for reliable attachment of the first organic molecule to the functional groups of the base polymer. More preferably, the attachment unit is an acid anhydride group or an acid chloride group, in particular an acid anhydride group.

The reaction of the first organic molecule with the functional groups of the base polymer are preferably conducted such that the attachment unit undergoes a reaction with the functional groups while the cross-linkable unit remains unchanged.

Various organic molecules may be used as first organic molecule. Advantageously, the first organic molecule is a molecule of the formula X—Y or X—R—Y, wherein X in each formula comprises an aldehyde group, an acid chloride group or an acid anhydride group, R is an optionally substituted hydrocarbon moiety with 2 to 10 carbon atoms, and Y in each formula comprises a carbon-carbon double bond, an epoxide group, or an acid anhydride group. Examples of hydrocarbon moieties are aromatic moieties derived from benzene such as —$C_6H_4$—, and aliphatic moieties such as —$C_nH_{2n}$—. The optional substituents include halide, straight or branched $C_1$ to $C_5$ alkyl residues and hydroxyl.

Preferably, the first organic molecule is selected from the group consisting of acrylic anhydride, acryloyl chloride, pent-4-enal, ethyl 2,3-epoxypropionate, methacrylic anhydride, methacryloyl chloride, mercaptopropionic acid, and maleic anhydride. In methacrylic anhydride, for example, X is $H_3C$—C(=$CH_2$)—C(=O)—O—C(=O)— and Y is —C(=$CH_2$)—$CH_3$. The aforementioned organic molecules allow for attachment to the base polymer thereby providing a cross-linkable unit.

The cross-linkable polymer according to the invention comprises a base polymer comprising functional groups at least some of which have been reacted with a second organic molecule capable of bonding to organic and/or inorganic substrates. Advantageously, the second organic molecule comprises a bonding unit. The bonding unit particularly provides the second organic molecule with the capability to bond to organic and/or inorganic substrates. Preferably, the bonding unit comprises at least one of a catechol group; a quinone group; a group of the formula —$SiX^1X^2X^3$, wherein $X^1$, $X^2$, and $X^3$ are independently selected from the group consisting of a halide, in particular chloride, methoxy, ethoxy, isopropoxy, and acetoxy; a thiol group; a phosphono group or its derivatives; a phosphate group or its derivatives; and a dicarboxyl group. It was found that these groups allow for good adhesion, in particular to organic and/or to inorganic substrates. The bonding unit may also consist of the aforementioned groups. More preferably, the bonding unit is a catechol group. The catechol was found to be particularly versatile.

Advantageously, the second organic molecule comprises a connecting unit. The connecting unit particularly allows the attachment, in particular the covalent attachment, of the second organic molecule to the functional groups of the base polymer. After reaction of the second organic molecule with a functional group of the base polymer, the connecting unit may be transformed into a different group. For example, the second organic molecule may comprise an acid chloride group as a connecting unit that may be transformed into an ester or an amide group upon reaction with a hydroxyl or an amine group as the functional groups of the base polymer. Preferably the connecting unit of the second organic molecule is selected from the group consisting of an aldehyde group, an acid chloride group, an acid anhydride group, a carboxylic acid group, an amine group, and a hydroxyl group. These units have shown to allow for reliable attachment of the second organic molecule to the functional groups of the base polymer. More preferably, the connecting unit is an amine group or and acid anhydride group, in particular an amine group.

Amine groups may also be present in the form of their conjugated acid in the second organic molecule.

The reaction of the second organic molecule with the functional groups of the base polymer are preferably conducted such that the connecting unit undergoes a reaction with the functional groups while the bonding unit remains unchanged.

Various organic molecules may be used as the second organic molecule. Advantageously, the second organic molecule is a molecule of the formula X'—R'—Y', wherein X' is an aldehyde group, an acid chloride group, an acid anhydride group, a carboxylic acid group, an amine group, or a hydroxyl group, R' is an optionally substituted hydrocarbon moiety with 2 to 10 carbon atoms, and Y' is a catechol group; a quinone group; a group of the formula —SiX$^1$X$^2$X$^3$, wherein X$^1$, X$^2$, and X$^3$ are independently selected from the group consisting of a halide, in particular chloride, methoxy, ethoxy, isopropoxy, and acetoxy; a thiol group; a phosphono group or its derivatives; a phosphate group or its derivatives; or a dicarboxyl group. Preferably, the second organic molecule is selected from the group consisting of 3,4-dihydroxyphenethylamine, aminopropyltriethoxysilane, and (2-aminoethyl)phosphonic acid, more preferably 3,4-dihydroxyphenethylamine.

The cross-linkable polymer particularly has a molecular weight of 500 kDa or less, preferably from 750 Da to about 500 kDa, more preferably from 10 kDa to 500 kDa. The molecular weight may be determined by gel permeation chromatography coupled with a multi-angle laser light scattering detector using phosphate buffered saline (pH 7.4) at an NaCl concentration of 0.15 mol/L as a solvent. Advantageously, the cross-linkable polymer is water-soluble.

The cross-linkable polymer comprises a base polymer comprising functional groups at least some of which have been reacted with a first organic molecule and with a second organic molecule. By reacting at least some of the functional groups of the base polymer with a first organic molecule, the functional groups of the base polymer are particularly functionalized with the first organic molecule. The degree of functionalization may vary. In principle, 0.1% to 99% of the functional groups of the base polymer may have reacted with the first organic molecule. Preferably, from 1% to 50%, more preferably 10% to 30%, of the functional groups of the base polymer have reacted with the first organic molecule. Thus, the degree of functionalization of the base polymer with the first organic molecule may be 0.1% to 99%, preferably 1% to 50%, more preferably 10% to 30%. With the degree of functionalization with the first organic molecule, the stiffness and the swelling ratio of the hydrogel may be adjusted. A higher degree of functionalization thereby leads to an increased stiffness after cross-linking. Since in a base polymer with different functional groups, not all of the functional groups of the base polymer may be reactive towards the first organic molecule, the degree of functionalization may in particular be determined with respect to only the functional groups or the type of functional group that are reactive towards the first organic molecule. For example in hyaluronic acid, only the primary alcohol functional group is considered reactive towards an anhydride such as methacrylic anhydride. In this case, the degree of functionalization of the base polymer would be determined with respect to the primary alcohol functional group.

By reacting at least some of the functional groups of the base polymer with a second organic molecule, the functional groups of the base polymer are particularly functionalized with the second organic molecule. The degree of functionalization may vary. In principle, 0.1% to 70% of the functional groups of the base polymer may have reacted with the second organic molecule. Preferably, from 1% to 30%, more preferably 10% to 30%, of the functional groups of the base polymer have reacted with the second organic molecule. Thus, the degree of functionalization of the base polymer with the second organic molecule vary may be 0.1% to 70%, preferably 1% to 30%, more preferably 10% to 30%. With the degree of functionalization with the second organic molecule, the number of groups capable of bonding with organic and/or inorganic substrates may be adjusted. A higher degree of functionalization thereby leads to a higher number of groups capable of bonding with organic and/or inorganic substrates. Since in a base polymer with different functional groups, not all of the functional groups of the base polymer may be reactive towards the second organic molecule, the degree of functionalization may in particular be determined with respect to only the functional groups or the type of functional group that are reactive towards the second organic molecule. For example in hyaluronic acid, only the carboxylic acid functional group is considered reactive towards an amine such as 3,4-dihydroxyphenethylamine. In this case, the degree of functionalization of the base polymer would be determined with respect to the carboxylic acid functional group.

According to an embodiment, the invention provides for a cross-linkable polymer comprising a base polymer comprising functional groups at least some of which have been reacted with a first organic molecule comprising a cross-linkable unit and with a second organic molecule capable of bonding to organic and/or inorganic substrates, wherein the base polymer is hyaluronic acid, the first organic molecule is a molecule of the formula X—Y or X—R—Y, wherein X in each formula comprises an aldehyde group, an acid chloride group or an acid anhydride group, R is an optionally substituted hydrocarbon moiety with 2 to 10 carbon atoms, and Y in each formula comprises a carbon-carbon double bond, an epoxide group, or an acid anhydride group, in particular wherein the first organic molecule is methacrylic anhydride or methacryloyl chloride, and the second organic molecule is a molecule of the formula X'—R'—Y', wherein X' is an aldehyde group, an acid chloride group, an acid anhydride group, a carboxylic acid group, an amine group, or a hydroxyl group, R' is an optionally substituted hydrocarbon moiety with 2 to 10 carbon atoms, and Y' is a catechol group; a quinone group; a group of the formula —SiX$^1$X$^2$X$^3$, wherein X$^1$, X$^2$, and X$^3$ are independently selected from the group consisting of a halide, in particular chloride, methoxy, ethoxy, isopropoxy, and acetoxy; a thiol group; a phosphono group or its derivatives; a phosphate group or its derivatives; or a dicarboxyl group, in particular wherein the second organic molecule is 3,4-dihydroxyphenethylamine. Preferably, the hydroxyl groups of the hyaluronic acid have been reacted with the first organic molecule, in particular with methacrylic anhydride or methacryloyl chloride. Preferably, the carboxyl groups of hyaluronic acid have been reacted with the second organic molecule, in particular with 3,4-dihydroxyphenethylamine.

The cross-linkable polymer particularly comprises cross-linkable polymer strands. More particularly, the cross-linkable polymer strands are the individual polymer molecules in the cross-linkable polymer. The cross-linkable polymer strands particularly provide at least one cross-linkable unit derived from the first organic molecule.

Organic substrates are preferably biological surfaces, in particular human or animal tissues, such as cartilage tissue, meniscus tissue, eye tissue, corneal tissue, skin, nucleus pulposus tissue, and cardiovascular tissue. Inorganic substrates are preferably biological surfaces, in particular human or animal tissues such as bone tissue.

The cross-linkable polymer according to the invention is particularly well suited for the formation of hydrogels. Accordingly, the invention also provides for a hydrogel comprising a cross-linkable polymer according to the invention comprising cross-linkable polymer strands, wherein at least some of the cross-linkable units of different cross-linkable polymer strands have reacted to form a covalent bond thereby forming a covalently linked network.

The hydrogel according to the invention may comprise one or more additives. Preferably, the hydrogel comprises at least one additive in particular selected from the group consisting of organic fillers, inorganic fillers, aramid fibers, cellulose fibers, poly(acrylates), poly(methacrylates), collagen fibers, silk fibers, chitin, chitosan, starch, nanoparticles, in particular silica, calcium phosphate, nanodiamond, and mixtures thereof. By the addition of fillers, composite networks may be formed in the hydrogel.

Advantageously, covalent links have been formed in the hydrogel, particularly by reaction of at least some of the cross-linkable units of the first organic molecule. By the covalent links, a covalent network may be formed in the hydrogel.

The organic residues that are covalently attached to the functional groups of the base polymer by reaction of the second organic molecule may form in the hydrogel non-covalent bonds, in particular with other organic residues derived from the second organic molecule or with the functional groups of the base polymer or with any additive present in the hydrogel. In this way, a non-covalent network may be formed. Preferably, a first portion of the organic residues derived from the second organic molecules forms non-covalent bonds with the functional groups of the base polymer and/or a second portion of the organic residues derived from the second organic molecules and/or the at least one additive. These non-covalent bonds may support network formation by the cross-linking of the cross-linkable units. In particular, different organic residues derived from the second organic molecule may form non-covalent bonds with different moieties. For example, a first portion of the organic residues derived from the second organic molecule may form non-covalent bonds with a second portion of organic residues derived from the second organic molecule, a third portion of organic residues derived from the second organic molecule may form non-covalent bonds with the functional groups of the base polymer, and a fourth portion of organic residues derived from the second organic molecule may form non-covalent bonds with the at least one additive if present. The skilled person will understand that different combinations of the bonding partners are possible.

Advantageously, the hydrogel comprises a liquid. Examples of liquids are water, buffer, phosphate buffered saline (PBS), hepes buffer, or alcohol. Preferably, the hydrogel comprises water or buffer. The hydrogel may comprise the liquid in the amount from 70 to 99 wt. %, preferably from 75 to 99 wt. %, more preferably from 80 to 99 wt. %, in each case based on the total weight of the hydrogel. Preferably, the hydrogel comprises water, buffer, phosphate buffered saline (PBS), hepes buffer, or alcohol, more preferably water, in particular in the amount from 70 to 99 wt. % or from 75 to 99 wt. % or from 80 to 99 wt. %, in each case based on the total weight of the hydrogel.

The hydrogel preferably has good mechanical properties. Preferably the mechanical properties of the hydrogel are tunable. Advantageously, the hydrogel has an elastic modulus from about 2 kPa to about 4 MPa. Elastic moduli in the aforementioned range allow to tailor the properties of the hydrogel to the requirements of the specific application.

On exposure to liquids, in particular to water or buffer, the hydrogel according to the invention may swell. The swelling ratio is calculated by the following formula Swelling ratio [%]=100*{(volume of the hydrogel after swelling)−(volume of the hydrogel before swelling)}/(volume of the hydrogel before swelling).

The hydrogel preferably has a swelling ratio from −20% to 150%. The swelling ratio may particularly be tuned in the aforementioned range. In this way, the swelling ratio may be adapted to the requirements of the specific application.

Advantageously, the hydrogel according to the invention adheres to various surfaces, in particular to organic surfaces, more particularly to biological surfaces. Preferably, the hydrogel adheres to different human or animal tissues, in particular adheres to at least one of cartilage tissue, meniscus tissue, eye tissue, in particular corneal tissue, skin, nucleus pulposus tissue, annulus fibrosus tissue, cardiovascular tissue, and bone tissue. Accordingly, the hydrogel according to the invention may be used for example in curing injuries of the aforementioned tissue or as an implant.

The invention also provides for a method for the preparation of a hydrogel, in particular of a hydrogel according to the invention, comprising the steps of
  a. providing a cross-linkable polymer according to the invention,
  b. dissolving the cross-linkable polymer in a solvent to obtain a solution,
  c. optionally, adding a cross-linking agent to the solution,
  d. cross-linking of the cross-linkable polymer by an external stimulus to obtain a hydrogel.

Different cross-linking agents may be used in the method according to the invention. Preferably, the cross-linking agent is biocompatible. This may allow for the use of the resulting hydrogel in biomedical applications.

The cross-linking agent is preferably selected from the group consisting of a radical initiator, an oxidating agent, and a diamine. More preferably, the cross-linking agent is a radical intiator. The cross-linking agent may particularly react with the cross-linkable units that are present in the cross-linkable polymer according to the invention, in particular due to the reaction of the functional groups of the base polymer with the first organic molecule. The cross-linking agent may need to be activated to react with the cross-linkable units. For example, a radical initiator that is activated by UV light may be used as a cross-linking agent. The cross-linking agent may be added as such or it may be added in the form of a solution. In particular, the cross-linking agent may be dissolved in the solution containing the cross-linkable polymer. For this purpose, the cross-linking agent may be added in the form of a solution.

Advantageously, the solvent in which the cross-linkable polymer according to the invention is dissolved is preferably a solvent that is later contained in the hydrogel. Accordingly, the solvent is preferably selected from water, buffer, phosphate buffered saline (PBS), hepes buffer, and alcohol. The concentration of the cross-linkable polymer in the solution is preferably from 1 to 30 wt. %, more preferably from 1 to 25 wt. %, even more preferably from 1 to 20 wt. %, based on the total weight of the solution. By varying the concentration of the cross-linkable polymer in the solution, the mechanical properties and the adhesive properties of the hydrogel may be tuned.

In the method according to the invention, cross-linking of the cross-linkable polymer is particularly effected by an external stimulus to obtain a hydrogel. The external stimulus may cross-link the cross-linkable polymer directly or it may activate the optional cross-linker. The cross-linking then occurs via the cross-linkable units that are present in the cross-linkable polymer according to the invention, in particular due to the reaction of the functional groups of the base polymer with the first organic molecule. Preferably, the external stimulus is selected from the group consisting of UV irradiation, X-ray irradiation, infrared irradiation, and heating.

The solution of the cross-linkable polymer may be further modified. For example, it has been found that it may be beneficial to degas the solution in a step prior to step d. In this way, side reactions may be suppressed. Moreover, an additive may be added to the solution prior to step d. The details of the additive of the hydrogel according to the invention apply accordingly to the details of the additive according to the method according to the invention. Preferably, the additive is dissolved in the solution. It is also possible that more than one additive is added to the solution prior to step d.

The invention also provides for a hydrogel obtainable according to the method according to the invention.

The invention also provides for the use of the cross-linkable polymer according to the invention for the preparation of a hydrogel.

The hydrogel according to the invention may be used for several purposes. For example, the hydrogel may be used in the treatment of cartilage damage, meniscus damage, corneal damage, nucleus pulposus or annulus fibrosus damage, cardiac tissue damage, bone tissue damage, dental tissue damage. In particular, the hydrogel may be used as an implant.

Accordingly, the invention provides for a hydrogel according to the invention for use in the treatment of cartilage damage, meniscus damage, corneal damage, nucleus pulposus or annulus fibrosus damage, cardiac tissue damage, bone tissue damage, dental tissue damage and/or as implant, in particular in surgery.

DESCRIPTION OF THE INVENTION

Examples

Materials

Figure 1:
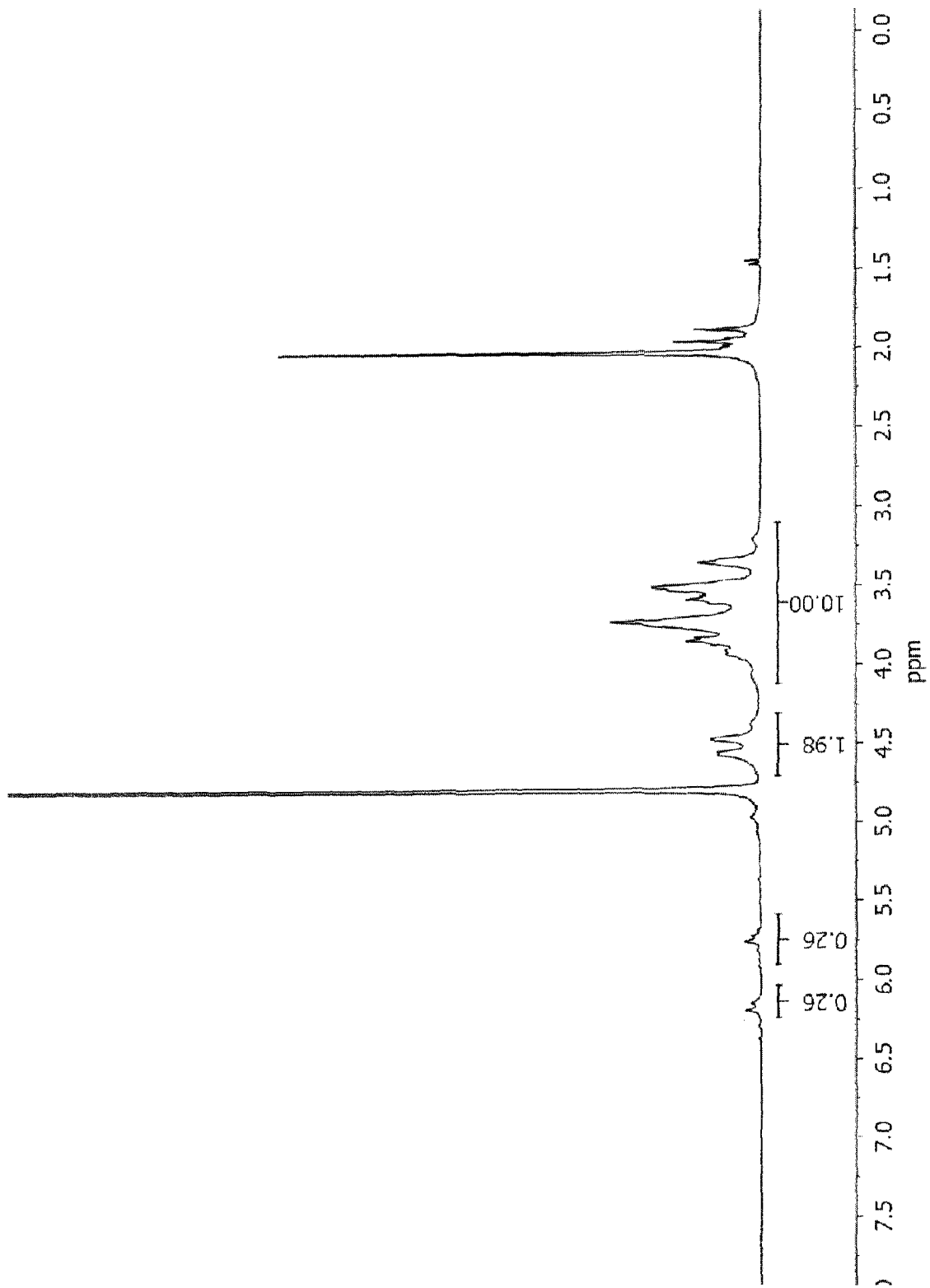
FIG. 1 shows an NMR spectrum of hyaluronic acid that was reacted with methacrylic anhydride as described in the examples section.

Sodium hyaluronate (hereinafter HA) of three different molecular weights (15-30 kDa, 50-90 kDa and 300-500 kDa) was purchased from Contipro a.s. (CZ). Methacrylic anhydride, sodium hydroxide, dialysis sacks (molecular weight cut-off 6000-8000 Da) and hydrochloric acid were purchased from Sigma-Aldrich. Dopamine hydrochloride (Dopa or Dopamine), N-(3-Dimethylaminopropyl)-N'-ethylcarbodiimide hydrochloride (EDC, purum, ≥98.0%) and deuterium oxide ($D_2O$) were purchased from Sigma-Aldrich. For radical polymerization, Irgacure 2959 (BASF) was used as photoinitiator. Nanofibrillated Cellulose (NFC) was provided by EMPA (Swiss Federal Laboratories for Materials Science and Technology, Dithendorf, Switzerland). Phosphate buffered saline with a concentration of 0.155 mol/L sodium chloride and 0.0041 mol/L phosphate (added in the form of $Na_2HPO_4$ and $KH_2PO_4$) with a pH of 7.4 was purchased from Thermo Fisher Scientific as "10010 PBS".

General Synthetic Procedures

Functionalization of Hyaluronic Acid with Methacrylic Anhydride and Dopamine (Hereinafter MeCHa) as a Cross-Linkable Polymer The synthesis of MeCHa was performed in two steps and is depicted schematically in Scheme 1. First, the methacrylation of HA was carried out in aqueous solution at alkaline pH and to the reaction product, catechol groups were subsequently attached by reaction with dopamine under acidic conditions. The order of the functionalization steps is important due to the synthesis pH conditions and in order to avoid deteriorating the dopamine adhesive performance.

Scheme 1 Synthetic route to MeCHa.

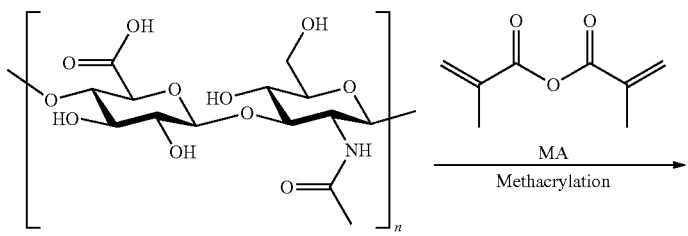

-continued

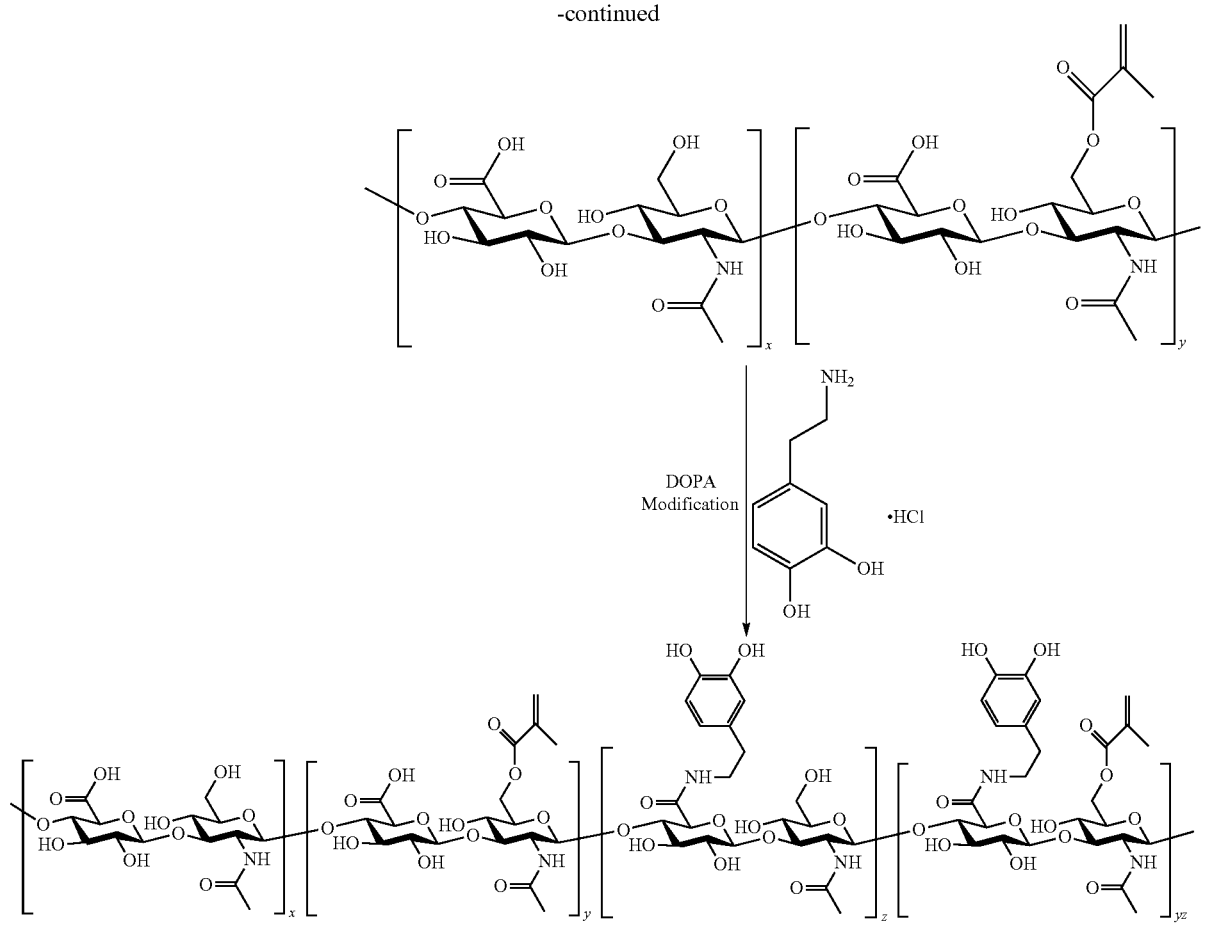

General Methacrylation Procedure 0.5 g of HA was dissolved in 50 ml (100 ml) of deionized water in a glass flask with a magnetic stir bar and stirred vigorously for 30 min at room temperature. The flask was then placed in an ice container and the temperature was kept at around 4° C. under a fume hood. While stirring, the pH of the HA solution was adjusted to 8.5 using 1.0 M NaOH.

Two different protocols (a and b) were followed in order to obtain two different methacrylation degrees:
 a) Low methacrylation degree. One dose of methacrylic anhydride (1.963 mL) was added dropwise to the solution and the pH was adjusted to 8±0.5 with 5N NaOH. The pH was adjusted every 5 minutes for 3 hours (it should be noted that the pH will not remain steady as it will have a tendency to acidify quite rapidly). Thereafter, a second dose of 1.963 mL methacrylic anhydride was added and the pH was adjusted to 8±0.5. The solution was stirred in the cold room at 4° C. overnight while the flask opening was covered with parafilm. Then, the pH was adjusted to 7.5±0.5 and the reaction solution was transferred to 50 mL conical tubes and spun for 5 min at 1200 g. Unreacted chemicals were removed by dialysis for three days and the dialysis water was changed 3 times daily.
 b) High methacrylation degree. 1.4 ml of methacrylic anhydride (1.035 g/mL) was added dropwise to the solution and the pH was adjusted to 8.5 repeatedly during the MA addition. The reaction was allowed to proceed on ice for 4 hours while maintaining the pH at 8.5-9.5. pH adjustment was performed continuously during the reaction, therefore the pH was not allowed to be less than 8.5. It should be also noted that adequate stirring is essential to generate an emulsion during the functionalization, as insufficient stirring leads to phase separation. Thereafter, the reaction was followed by a second addition of 1.4 ml of methacrylic anhydride for another 4 hours. The solution was then stirred vigorously overnight at room temperature when the pH was stable after the 8 hours of modification. Unreacted chemicals were removed by dialysis (6-8 kDa dialysis membrane tubing) for three days and the dialysis water was changed twice daily.

After dialysis, the solution was transferred to 50 ml tubes in 25-30 ml aliquots and frozen in a −80° C. freezer overnight. Afterwards, the samples were lyophilized for three days. The tubes were transferred in dry ice and covered with a kimwipe before lyophilization.

General Dopamine Functionalization Procedure

The reaction of hyaluronic acid with Dopa was conducted using N-(3-Dimethylaminopropyl)-N'-ethylcarbodiimide hydrochloride (EDC) as an activation agent of the carboxyl groups on the hyaluronic acid. The reaction was performed at room temperature under nitrogen atmosphere and pH control in order to avoid the irreversible oxidation of dopamine molecules. Briefly, 0.5 g of methacrylated HA was dissolved in 50 ml of phosphate buffered saline (PBS) solution in a three-neck round-bottom flask with a magnetic stir bar and the pH was adjusted to 5.5 using hydrochloric acid (HCl). The solution was then purged with nitrogen for one hour. Then, 175 mg of EDC and 240 mg of dopamine hydrochloride were added into the reaction mixture and the pH of the reaction solution was maintained at 5.5 for 150 minutes. The functionalization process was performed under nitrogen atmosphere. The reaction mixture was afterwards dialyzed using dialysis tubes (6-8 kDa dialysis membrane tubing) against acidic water with pH of around 5.5 for three days until all unreacted chemicals were removed. The dialysis water was changed twice daily. It should be noted that further purification can also be carried out by another dialysis in deionized water. The samples were finally frozen in a −80° C. freezer overnight, covered with a kimwipe and lyophilized for three days. The modified MeCHa was stored at 4° C. under vacuum and protected from the light.

General Hydrogel Synthesis Procedure

The MeCHa hydrogel was synthesized by dissolving the lyophilized MeCHa polymer as hydrogel precursor in phosphate buffered saline (PBS, pH 7.4) (at a concentration of 4.8 wt %) followed by dissolving Irgacure 2959 (0.1%, w/v) in the resulting solution. The hydrogel precursor was homogenized using vortex and the degassed mixture was then poured into molds made of Teflon and covered with microscope slides. The mixtures containing the MeCHa molecules in the molds were irradiated with ultraviolet irradiation with the wavelength of 365 nm, a light intensity of 5 mW·cm$^{-2}$ for 10 minutes to cross-link the MeCHa polymer strands.

The hydrogel from methacrylated hyaluronic acid was synthesized (to serve as comparative example) by dissolving 4.8 wt % of the lyophilized methacrylated hyaluronic acid as hydrogel precursor in phosphate buffered saline (PBS, pH 7.4) followed by dissolving Irgacure 2959 (0.1%, w/v) in the resulting solution. The hydrogel precursor was homogenized using vortex and the degassed mixture was then poured into molds made of Teflon and covered with microscope slides. The precursor was irradiated with ultraviolet irradiation as described above.

Poly(ethylene glycol)dimethacrylate (hereafter "PEGDMA") and nanofibrillated cellulose (NFC)-reinforced double-network PEGDMA-alginate hydrogels were also prepared using the same procedure (to serve as comparative examples). PEGDMA hydrogels were synthesized as a hydrogel with 95.2 wt % water content and with 4.8 wt % PEGDMA. Composite hydrogels were synthesized with 4.8 wt % PEGDMA, 0.55 wt % sodium alginate and 0.5 vol. % NFC, which gives 94 wt % water content. The composite hydrogel precursor was synthesized by mixing PEGDMA, calcium sulphate, NFC (0.5 vol %), and Irgacure 2959 (0.1%, w/v) in distilled water. The hydrogel precursor was homogenized using an Ultra-Turrax at 12000 rpm for 20 min and sodium alginate was added. The PEGDMA molecules were crosslinked by ultraviolet irradiation with the wavelength of 365 nm, with a light intensity of 5 mW·cm$^{-2}$ for 30 minutes.

Characterization

Nuclear Magnetic Resonance (NMR) Analysis. The degree of functionalization for methacrylated polymers and MeCHa polymers was analyzed using $^1$H NMR spectroscopy with D$_2$O as the solvent using a 400 MHz Bruker Avance NEO. Briefly, 10 mg of the modified polymers was dissolved in 600 μl of D$_2$O at room temperature. The solutions were then transferred to NMR tubes and sealed with a cap. The same procedure was used for methacrylated hyaluronic acid (control samples) as well.

Swelling ratio and water content study. The swelling ratios of a MeCHa-Gel and of methacrylated HA with high and low methacrylation degree, as well as PEGDMA-based hydrogels including single network and composite double-network hydrogels were evaluated in both PBS and distilled water at room temperature. Circular hydrogel samples were obtained using molds with a diameter of 4.6 mm and a depth of 2.4 mm following the general hydrogel synthesis procedure. After irradiation, the hydrogels were removed from the molds and immersed into distilled water or PBS solution, respectively, for 24 h. The swelling ratio (SR) was calculated with the following equation: $SR(\%)=(Vs-V0)/V0\times100$, where V0 is the volume of the samples before swelling and Vs is the volume of the samples after swelling.

Tissue preparation. For the adhesion test, tissue samples were prepared in cylindrical shape with a diameter of 6.6 mm and a height of 10 mm from bovine articular cartilage on femoro-patellar groove.

Mechanical characterization—unconfined compression and hydrogel-tissue adhesion measurement. After placing the tissue samples into a two-piece mold, the hydrogel precursors were poured onto the prepared samples in the mold and photopolymerized on the top of the tissue surface. The two-piece mold was removed after polymerization and the attached tissue was quickly gripped for the adhesion test. Adhesion measurement was performed using an Instron E3000 linear mechanical testing machine (Norwood, MA, United States) with a 50 N load cell and a constant speed of 0.15 mm·s$^{-1}$. The adhesion strength was determined by dividing the maximum adhesion force by the surface area of the hydrogel-tissue contact.

Figure 2:
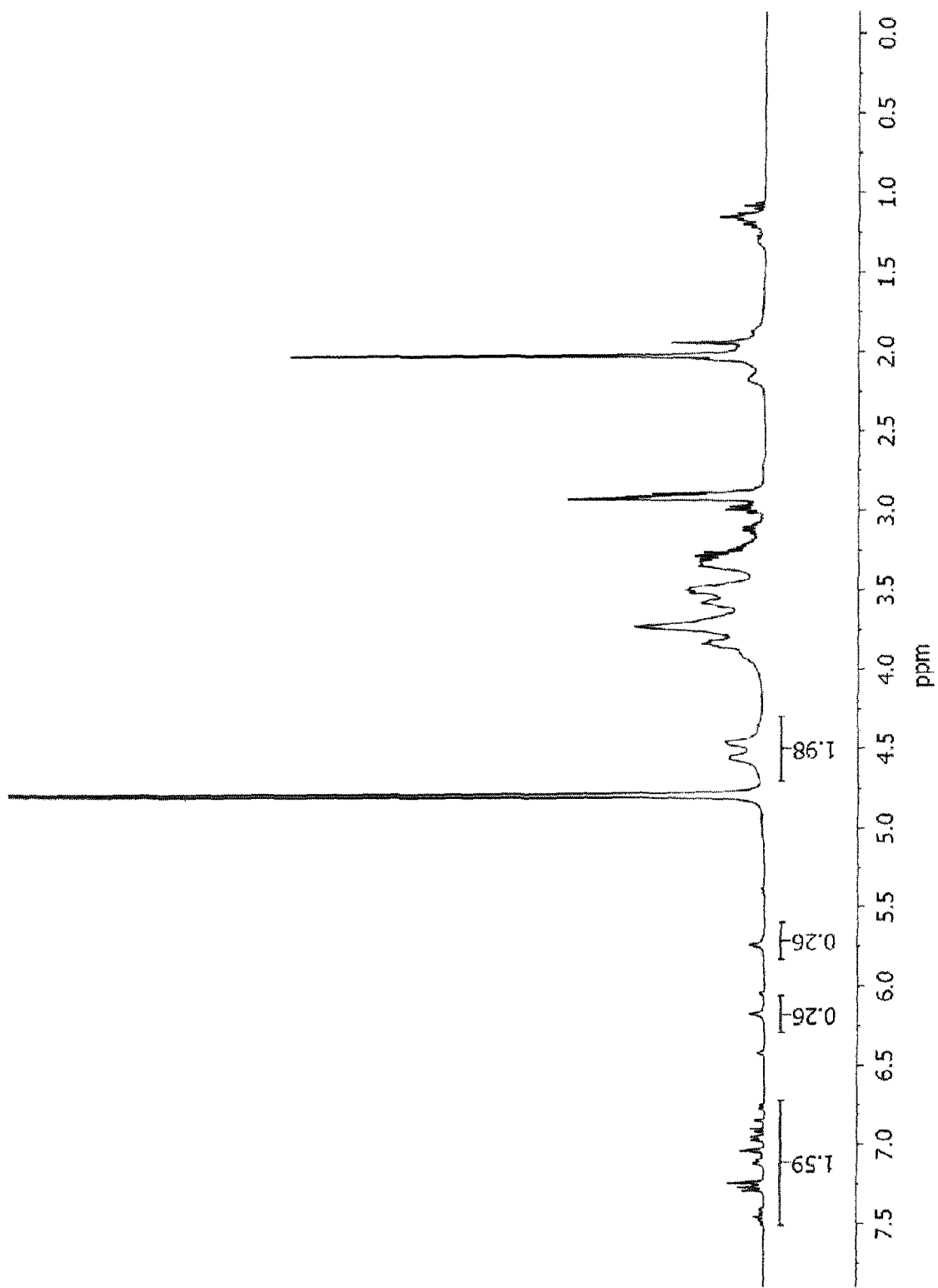
FIG. 2 shows an NMR spectrum of hyaluronic acid that was reacted with methacrylic anhydride and with dopamine hydrochloride as described in the examples section.

To evaluate the synthesis of the modified polymer, the chemical structure of MeCHa was analyzed by $^1$H NMR spectroscopy. FIG. 1 shows the spectrum of methacrylated HA with a hyaluronic acid molecular weight of 50-90 kDa as a representative $^1$H NMR spectrum of methacrylated HA. The hydroxyl group peaks are located at the chemical shift of 4.4-4.6 ppm. The degree of methacrylation was determined by integrating the peak area of the protons in the vinyl groups at the chemical shift of δ=5.8 and δ=6.25 ppm, relative to the carbohydrate methyl protons in the hyaluronic acid backbone at δ=3.2-4.2 ppm. Each vinyl group peak corresponds to one proton and the peaks corresponding to the hyaluronic acid backbone correspond to 10 protons. FIG. 2 shows the $^1$H NMR spectrum of MeCHa with a hyaluronic acid molecular weight of 50-90 kDa as a representative $^1$H NMR spectrum of MeCHa. The multiplets at the chemical shifts of δ=6.7-7 ppm in the MeCHa spectrum correspond to the protons in ortho and meta coupling position of the phenyl ring of Dopa and multiplet signals at δ=2.87 ppm and δ=3.22 ppm correspond to the protons of the aliphatic ethylene group. The grafting degree of Dopa per unit of hyaluronic acid was evaluated by comparison of the integrated peak areas of aromatic protons of Dopa at the chemical shift of 6.7-7.5 ppm relative to the carbohydrate methyl protons in the hyaluronic acid backbone at δ=3.2-4.2 ppm. The sharp peak at the chemical shift of 4.79 ppm in the NMR spectra is associated with D$_2$O.

From the $^1$H NMR analysis, the successful methacrylation and Dopa conjugation of the polymer backbone can be observed and a 26% methacrylation degree can be determined. As indicated in Scheme 1, the primary alcohol in hyaluronic acid is functionalized by the methacrylic anhydride. Since only the primary alcohol is considered reactive towards methacrylic anhydride, the degree of functionalization is determined only with respect to the primary alcohol functional groups of hyaluronic acid. The same procedure was performed for MeCHa polymer that was synthesized with a high methacrylation degree (approaching 99%, molecular weight of 50-90 kDa, hereinafter "~100% MeCHa 50-90 kDa"). The degree of functionalization with Dopa was about 15%. Since only the carboxylic acid group is considered reactive towards Dopa, the degree of functionalization is determined only with respect to the carboxylic acid functional groups of hyaluronic acid.

Thus, the following hydrogels were synthesized with the hydrogels using PEGDMA, NFC-PEGDMA-alginate, and the only methacrylated hyaluronice acid being comparative examples:

TABLE 1

Hydrogels prepared

| Hydrogel name | cross-linkable polymer (concentration) | Molecular weight of cross-linkable polymer | Degree of functionalization | Additives |
|---|---|---|---|---|
| PEGDMA* | PEGDMA (4.8 wt. %] | 20 kDa | NA | NA |
| NFC-PEGDMA-alginate* | PEGDMA (4.8 wt | 20 kDa | NA | 0.5 vol. % NFC fibers; 0.55 wt % alginate |
| 26% Methacrylated HA 50-90 kDa* | Hyaluronic acid functionalized by reaction with methacrylic anhydride | 50-90 kDa | 26% methacryloyl | NA |
| 26% MeCHa 50-90 kDa | Hyaluronic acid functionalized by reaction with methacrylic anhydride and by reaction with dopamine | 50-90 kDa | 26% methacryloyl; 15% Dopa | NA |
| ~100% Methacrylated HA 50-90 kDa* | Hyaluronic acid functionalized by reaction with methacrylic anhydride | 50-90 kDa | Approximately 99% methacryloyl | NA |
| ~100% MeCHa 50-90 kDa | Hyaluronic acid functionalized by reaction with methacrylic anhydride and by reaction with dopamine | 50-90 kDa | Approximately 99% methacryloyl; approximately 15% Dopa | NA |

*= comparative example;
NA = not applicable

Swelling Ratio and Water Content

Figure 3:
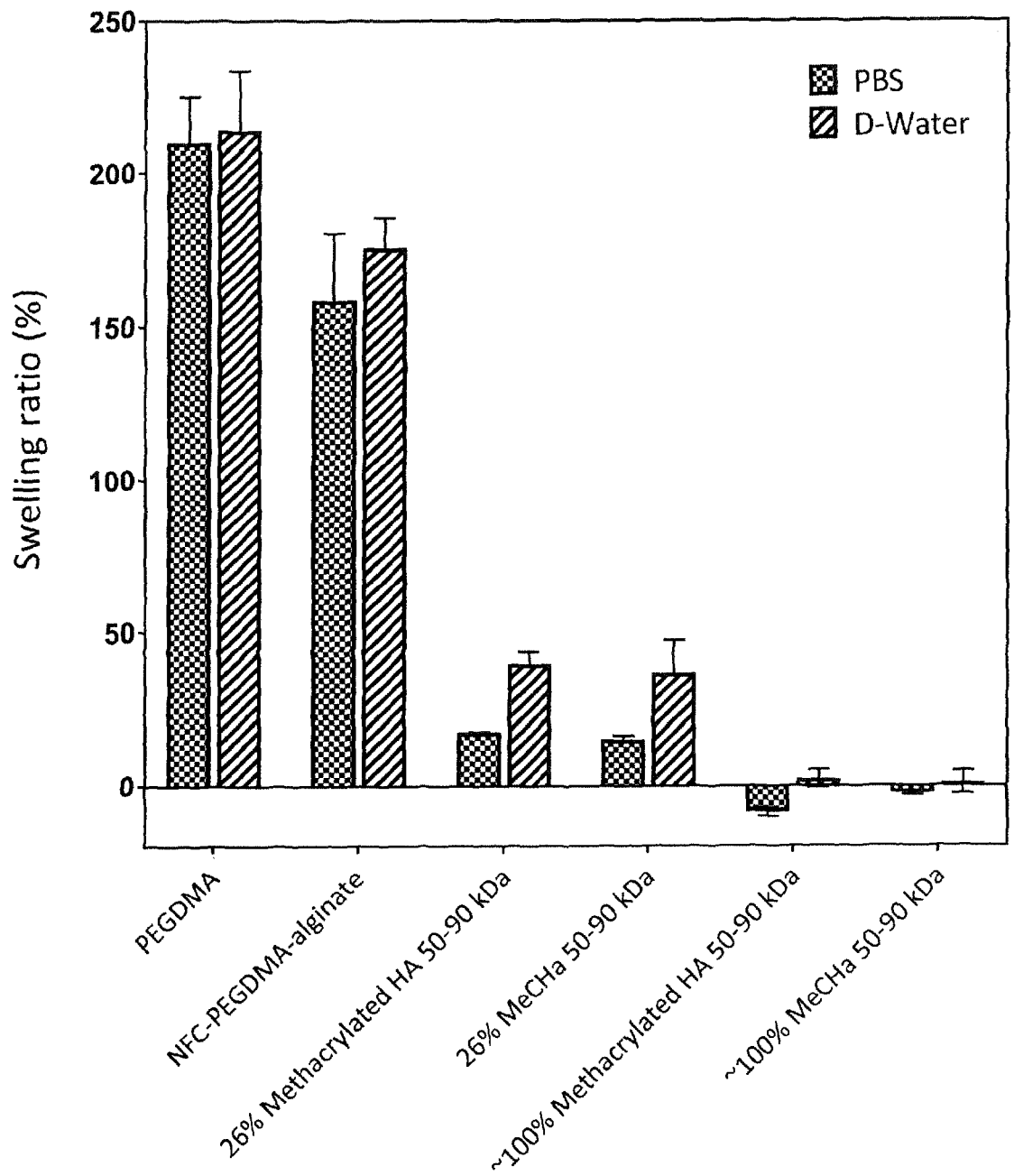
FIG. 3 shows the swelling ratio of different hydrogels.

All hydrogels are synthesized with a PBS buffer content of 95.2% except for the NFC-PEGDMA-alginate hydrogels that had a buffer content of 94%. FIG. 3 demonstrates the swelling behaviour of the hydrogels in both PBS and distilled water. The PEG-dimethacrylate based hydrogels present high swelling ratios. It should be noted that PEGDMA-based hydrogels with higher molecular weights display higher swelling ratios (not shown), presumably because the lower crosslink density and network configuration lead to higher chain mobility.

The methacrylated HA hydrogels generally show lower swelling ratios than PEGDMA-based hydrogels. However, the swelling is conspicuously higher in distilled water than in PBS for both PEGDMA-based and methacrylated HA hydrogels. The MeCHa-Gels present a much lower swelling ratio than the other hydrogel systems. For MeCHa with high methacrylation degree, the swelling ratio is quite negligible.

The synthesized hydrogels swell by a wide range and a slight shrinkage is also observed in methacrylated HA hydrogels with higher methacrylation degree. This implies that the swelling ratio of MeCHa-Gel can be tuned by alternating the modification degree, crosslink density and network configuration.

Mechanical Stiffness

To investigate the potential of the hydrogel design for tunable elastic performance, the mechanical stiffness of the synthesized hydrogels was evaluated and compared. For hydrogels based on functionalized hyaluronic acid, only the samples with a molecular weight of the hyaluronic acid of 50-90 kDa were investigated. The values are reported for the hydrogels in swollen state (in PBS and D-water). Hydrogels were compressed to 20% strain with a constant rate of 0.15 mm·s$^{-1}$.

Figure 4:
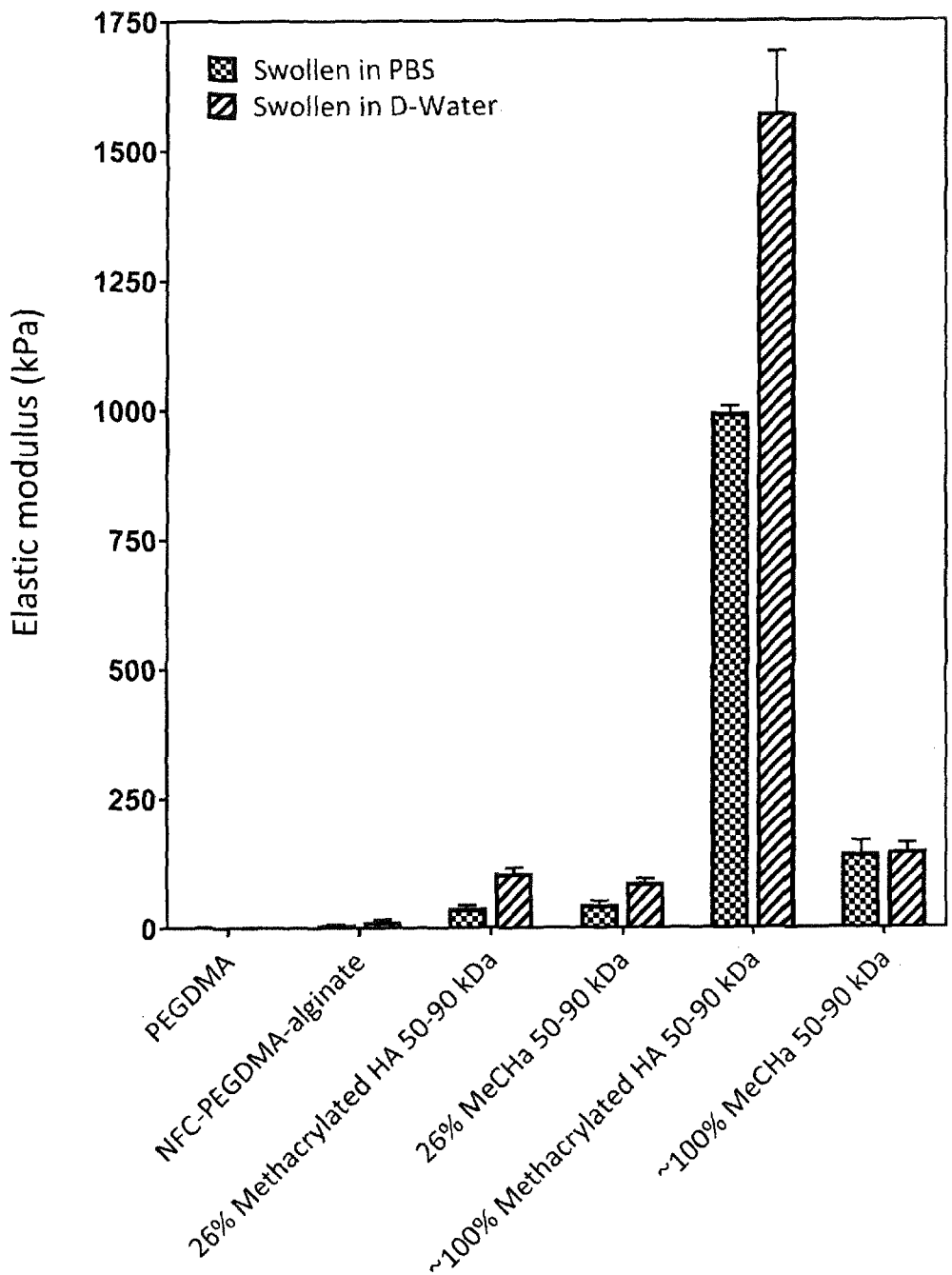
FIG. 4 shows the elastic modulus of different hydrogels.

The MeCHa-Gel has a conspicuously higher compression modulus than the PEGDMA and the composite PEGDMA hydrogels. It was found that the swollen MeCHa shows a much higher stiffness even than dry PEGDMA-based hydrogels. It is believed that the significant increase of the elastic modulus is achieved by the controllable cross-link density and chains configuration. FIG. 4 demonstrates the effect of methacrylation degree and Dopa conjugation on the mechanical stiffness of the synthesized hydrogel. It is observed that there is a dramatic increase in the elastic modulus of the hydrogel with the high methacrylation degree of backbone (~1 MPa). Moreover, while the modified hydrogels with low methacrylation degree (26%) are stiffer than PEGDMA-based hydrogels, they present significantly lower elastic moduli than hydrogels with high degree of methacrylation. Although the hydrogel sample 100% MeCHa 50-90 kDa with a high methacrylation degree has comparatively a very high stiffness, it shows a lower value than that of the methacrylated HA hydrogel without Dopa modification. On the other hand, there is a slight difference between the elastic moduli of the low methacrylated HA hydrogels (26%) with/without Dopa modification (samples 26% Methacrylated HA 50-90 kDa and 26% MeCHa 50-90 kDa). Moreover, it is observed that all swollen hydrogels demonstrate a higher stiffness in distilled water than in PBS (PH=7.4), while they present even higher swelling in distilled water.

Cartilage-MeCHa-Gel Adhesion

Figure 5:
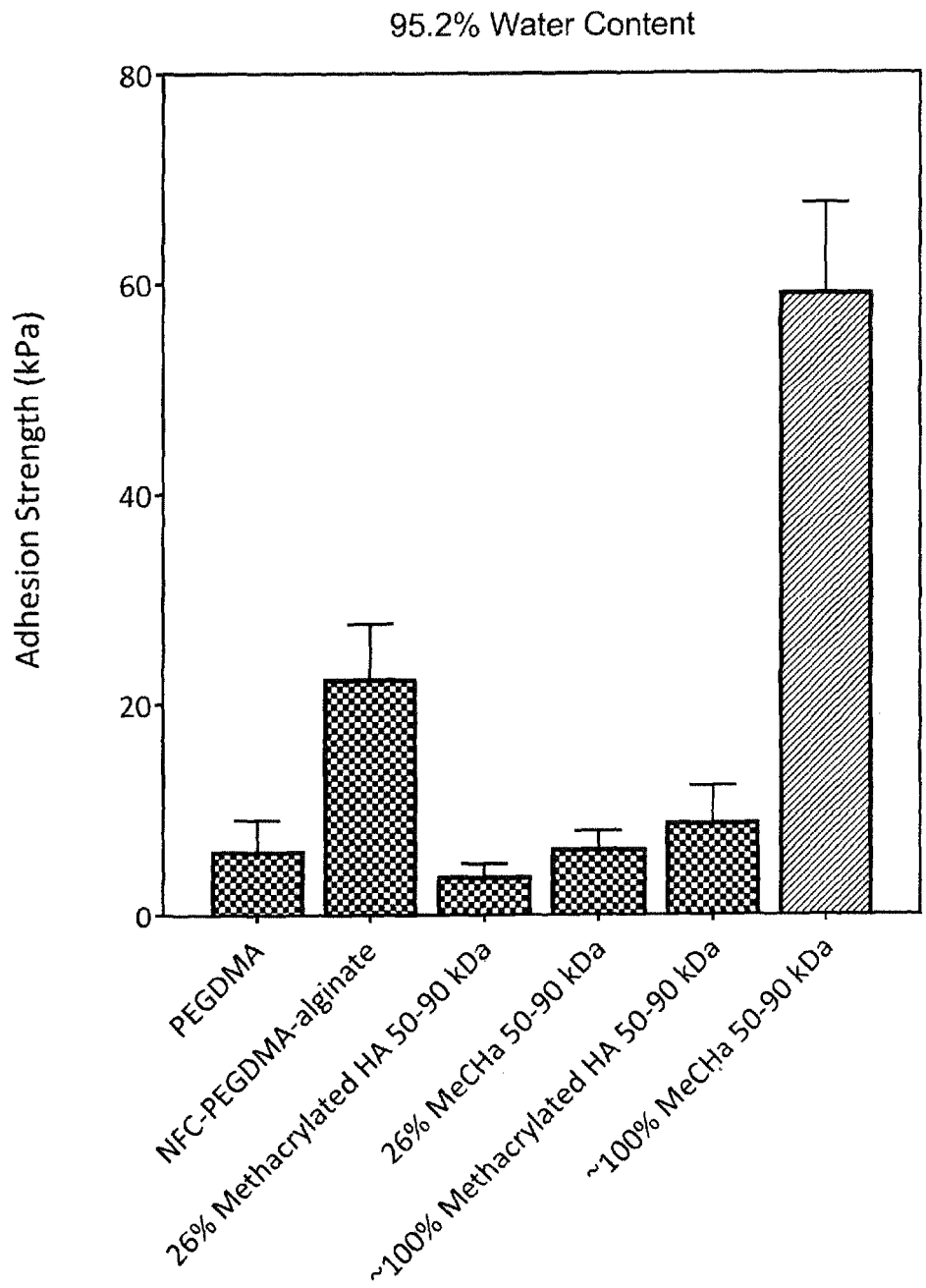
FIG. 5 shows the adhesion strength of different hydrogels.

To evaluate the adhesion performance of the synthesized hydrogel, a tissue-hydrogel adhesion test for various hydrogels with high water content of 95.2 wt. % was performed. For hydrogels based on functionalized hyaluronic acid, only the samples with a molecular weight of the hyaluronic acid of 50-90 kDa were investigated. FIG. 5 shows the adhesion strength of the synthesized PEGDMA-based hydrogels, methacrylated HA and MeCHa-Gel on bovine articular cartilage. The stiff and adhesive MeCHa-Gel (sample 100% MeCHa 50-90 kDa) has a significant increase in adhesion strength. It is believed that this is due to the attachment of a polymeric network containing both covalent crosslinks and adhesive components on the polymer backbone chains, which enable the hydrogel to be covalently attached to the tissue surface, without any surface modification, and also form a stiff network with covalent crosslinking. As a single network hydrogel, MeCHa-Gel presents a much higher adhesion than other single network hydrogels with the same water content, for example the sample PEGDMA or the sample 26% Methacrylated HA 50-90 kDa. In addition, the MeCHa-Gel is considerably more adhesive to the tissue than the composite double-network hydrogels (sample NFC-PEGDMA-alginate).

It appears that both the interfacial bonds and the bulk properties of the hydrogel are the significant contributing factors in order to achieve a high adhesive contact. The critical role of the adhesive component (Dopa) can be seen by comparing the adhesion between the samples 26% Methacrylated HA 50-90 kDa and 26% MeCHa 50-90 kDa. It shows the potential of the adhesive component for creating strong interfacial interactions. On the other hand, these interactions cannot present a high adhesion strength for a hydrogel with low mechanical stiffness (compare samples 26% MeCHa 50-90 kDa and 100% MeCHa 50-90 kDa). Indeed, both interfacial interactions and bulk mechanical properties appear to be required to be acting in concert for an adhesive hydrogel system.

The hydrogels according to the invention have several advantages: very low and tunable swelling, very high stiffness and unprecedented adhesion performance, all with high water content (95.2 wt %). Moreover, the hydrogels according to the invention show high adhesion while they may have a single network structure. The high adhesion is obtained without the need for a surface modification.

With the invention, a hydrogel with good adhesive properties and tunable bulk properties through can be prepared. The hydrogels according to the invention allow to combine a high stiffness and good adhesion with unique bulk and adhesive properties including adhesion in high water content, high stiffness and tunable swelling behavior.

The invention claimed is:

1. A cross-linkable polymer comprising a base polymer comprising functional groups at least some of which have been reacted with a first organic molecule comprising a cross-linkable unit and with a second organic molecule capable of bonding to organic and/or inorganic substrates, wherein the first organic molecule is selected from the group consisting of acrylic anhydride, acryloyl chloride, pent-4-enal, ethyl 2,3-epoxypropanoate, methacrylic anhydride, methacryloyl chloride, mercaptopropionic acid, and maleic anhydride.

2. The cross-linkable polymer according to claim 1, wherein the functional groups of the base polymer comprise at least one of hydroxyl groups, amine groups, carboxylic acid groups, amide groups, and thiol groups.

3. The cross-linkable polymer according to claim 1, wherein the base polymer is selected from the group consisting of hyaluronic acid, alginate, chitosan, pectine, poly (ethylene glycol), carboxymethyl cellulose, poly(vinyl alcohol), poly(2-hydroxyethyl methacrylate), poly(acrylamide), fibrin, silk, collagen, and mixtures thereof.

4. The cross-linkable polymer according to claim 1, wherein the cross-linkable unit of the first organic molecule comprises at least one of a carbon-carbon double bond (—C=C—), a thiol group (—SH), an epoxide group, and an acid anhydride group.

5. The cross-linkable polymer according to claim 1, wherein the first organic molecule comprises an attachment unit that allows the attachment of the first organic molecule to the functional groups of the base polymer.

6. The cross-linkable polymer according to claim 1, wherein the second organic molecule comprises a bonding unit that comprises at least one of a catechol group; a quinone group; a group of the formula —SiX$^1$X$^2$X$^3$, wherein X$^1$, X$^2$, and X$^3$ are independently selected from the group consisting of a halide, methoxy, ethoxy, isopropoxy, and acetoxy; a thiol group; a phosphono group or its derivatives; a phosphate group or its derivatives; and a dicarboxyl group.

7. The cross-linkable polymer according to claim 1, wherein the second organic molecule comprises a connecting unit that allows the attachment of the second organic molecule to the functional groups of the base polymer.

8. The cross-linkable polymer according to claim 1, wherein the second organic molecule is a molecule of the formula X'—R'—Y', wherein X' is an aldehyde group, an acid chloride group, an acid anhydride group, a carboxylic acid group, an amine group, or a hydroxyl group, R' is an optionally substituted hydrocarbon moiety with 2 to 10 carbon atoms, and Y' is a catechol group; a quinone group; a group of the formula —Six$^1$X$^2$X$^3$, wherein X$^1$, X$^2$, and X$^3$ are independently selected from the group consisting of a halide, methoxy, ethoxy, isopropoxy, and acetoxy; a thiol group; a phosphono group or its derivatives; a phosphate group or its derivatives; or a dicarboxyl group and/or wherein the second organic molecule is selected from the group consisting of 3,4-dihydroxyphenethylamine and aminopropyltriethoxysilane.

9. The cross-linkable polymer according to claim 1, wherein the cross-linkable polymer has a molecular weight less than 500 kDa and/or is water-soluble.

10. The cross-linkable polymer according to claim 1, wherein from 0.1% to 99% of the functional groups of the base polymer have reacted with the first organic molecule.

11. The cross-linkable polymer according to claim 1, wherein from 0.1% to 70% of the functional groups of the base polymer have reacted with the second organic molecule.

12. A hydrogel comprising the cross-linkable polymer according to claim 1, further comprising cross-linkable polymer strands, wherein at least some of the cross-linkable units of different cross-linkable polymer strands have reacted to form a covalent bond thereby forming a covalently linked network.

13. The hydrogel according to claim 12, wherein the hydrogel comprises at least one additive.

14. The hydrogel according to claim 12, wherein the hydrogel comprises water, buffer, phosphate buffered saline (PBS), hepes buffer, or alcohol.

15. The hydrogel according to claim 12, wherein the hydrogel has an elastic modulus from about 2 kPa to about 4 MPa.

16. The hydrogel according to claim 12, wherein the hydrogel has a swelling ratio from −20% to 150%.

17. The hydrogel according to claim 12, wherein the hydrogel adheres to different human or animal tissues.

18. A method for the preparation of a hydrogel, comprising the steps of
  a. providing the cross-linkable polymer according to claim 1,
  b. dissolving the cross-linkable polymer in a solvent to obtain a solution,
  c. optionally, adding a cross-linking agent to the solution,
  d. cross-linking of the cross-linkable polymer by an external stimulus to obtain a hydrogel.

19. The method according to claim 18, wherein the cross-linking agent is biocompatible.

20. The method according to claim 18, wherein the cross-linking agent is selected from the group consisting of a radical initiator, an oxidating agent, and a diamine.

21. The method according to claim 18, wherein the solvent is selected from water, buffer, phosphate buffered saline (PBS), hepes buffer, and alcohol.

22. The method according to claim 18, wherein the external stimulus is selected from the group consisting of UV irradiation, X-ray irradiation, infrared irradiation, and heating.

23. The method according to claim 18, wherein the solution is degassed in a step prior to step d.

24. The method according to claim 18, wherein an additive is added to the solution prior to step d.

25. The method according to claim 18, wherein the concentration of the cross-linkable polymer is from 1 to 30 wt. %.

26. The hydrogel according to claim 12 for use in the treatment of cartilage damage, meniscus damage, corneal damage, nucleus pulposus or annulus fibrosus damage, cardiac tissue damage, bone tissue damage, dental tissue damage and/or as implant.

* * * * *